United States Patent [19]

Rieger et al.

[11] Patent Number: 4,762,930

[45] Date of Patent: Aug. 9, 1988

[54] PROCESS FOR THE PREPARATION OF THE ALUMINUM SALT OF SACCHARIN

[75] Inventors: Martin M. Rieger; Robert K. Yang, both of Morris Plains, N.J.

[73] Assignee: Warner-Lambert Company, Morris Plains, N.J.

[21] Appl. No.: 635,318

[22] Filed: Jul. 27, 1984

Related U.S. Application Data

[62] Division of Ser. No. 329,644, Dec. 11, 1981, abandoned.

[51] Int. Cl.$^4$ ............................................. C07F 5/06
[52] U.S. Cl. ...................................... 548/108; 426/3
[58] Field of Search ............................... 548/101, 108

[56] References Cited

U.S. PATENT DOCUMENTS

| | | | |
|---|---|---|---|
| 2,932,659 | 4/1960 | Orthner et al. | 260/448 AD |
| 3,184,490 | 5/1965 | Davison et al. | 548/108 X |
| 4,071,526 | 1/1978 | Dotzer et al. | 548/101 |
| 4,342,774 | 8/1982 | Okabe et al. | 548/104 |

FOREIGN PATENT DOCUMENTS 0014476  4/1972  Japan ................................. 548/108

OTHER PUBLICATIONS

The Merck Index, 9th ed., Merck & Co., Rahway, N.J. (1976), p. 1077.

*Primary Examiner*—Donald G. Daus
*Assistant Examiner*—Diana G. Rivers
*Attorney, Agent, or Firm*—Charles A. Gaglia, Jr.; Gary M. Nath

[57] ABSTRACT

The aluminum salt of saccharin and a method for its preparation are disclosed. Chewing gum compositions comprising the novel salt are prepared.

4 Claims, No Drawings

PROCESS FOR THE PREPARATION OF THE ALUMINUM SALT OF SACCHARIN

This is a division of application Ser. No. 329,644 filed Dec. 11, 1981, now abandoned.

BACKGROUND OF THE INVENTION

Chewing gums which contain saccharin either alone or in combination with other natural or artificial sweeteners are well known. The saccharin is usually present in the chewing gum formulation in the form of a water-soluble salt, e.g., the sodium salt. Upon mastication of such a chewing gum which contains a water-soluble saccharin salt, one perceives an initial burst of sweetness which rapidly declines and is soon noticed to disappear. This leaves a no longer sweet piece of chewing gum which is usually disposed of in short order by the user. In order to prolong saccharin's sweetening effect, it has been proposed to utilize saccharin in a less soluble form. The use of one such form, the free acid form of saccharin, has met with only limited success since this material is still too water-soluble and is, therefore, rapidly lost from the bolus during mastication. We have now discovered that chewing gums comprising the aluminum salt of saccharin possess an unexpectedly prolonged period of sweetness retention when compared to similar chewing gum formulations containing other forms of saccharin.

SUMMARY OF THE INVENTION

The invention sought to be patented in its principle composition aspect is a chewing gum composition which comprises the aluminum salt of saccharin.

The invention sought to be patented in its principle method aspect is a method for producing an artificially sweetened chewing gum composition having prolonged sweetness retention, which method comprises the use of the aluminum salt of saccharin to sweeten said chewing gum.

The invention sought to be patented in its principle chemical composition aspect is the aluminum salt of saccharin.

The invention sought to be patented in its principle chemical process aspect is a process for preparing the aluminum salt of saccharin which comprises reacting the free acid form of saccharin with an aluminum alkoxide.

DESCRIPTION OF THE PREFERRED EMBODIMENTS

Many salts of saccharin are known, however, no reference has been found which describes the aluminum salt of saccharin.

The aluminum salt of saccharin may be prepared by any of several procedures. In one such procedure, the free acid form of saccharin is contacted with an aluminum alkoxide in a suitable non reactive solvent. The aluminum salt is thereafter isolated and purified by standard procedures. Any aluminum alkoxide may be utilized, aluminum isopropoxide is preferred. In the preferred method of preparation, the aluminum isopropoxide is dissolved in hot isopropyl alcohol, the solution is filtered to remove any insolubles and is then added directly to a solution of the free acid form of saccharin in isopropyl alcohol. The combined solution is refluxed, during which time a white precipitate is formed. The solution is allowed to cool and the precipitate is collected by filtration. The precipitate is washed with isopropyl alcohol and subsequently dried in vacuo at elevated temperature. The aluminum salt of saccharin, so produced, is used in preparing the chewing gum composition of the invention and may also be used for other purposes in which slow and continuous release of sweetness is desirable.

The alkoxide portion of the aluminum alkoxides contemplated by the invention comprises those having carbon chains of about 1 to 6 carbon atoms. The chains may be either straight or branched. Examples of such alkoxides are methoxide, ethoxide, isopropoxide, hexoxide and the like.

In general, the chewing gum compositions of the invention are prepared using standard ingredients and standard procedures and processing equipment. Since the aluminum salt of saccharin is novel, it, of course, cannot be considered a standard chewing gum ingredient. The method of incorporating this novel ingredient in chewing gum formulations, however, is within the skill of the art. Thus, the aluminum salt of saccharin is added to a standard chewing gum composition in an amount sufficient to provide an acceptably sweet chewing gum. This amount is readily ascertained by those skilled in the art. The aluminum salt of saccharin may be utilized alone or in combination with other known natural and artificial sweeteners.

The chewing gum compositions comprising the aluminum salt of saccharin unexpectedly have been found to possess a prolonged sweetness retention when compared to prior art chewing gum formulations which do not contain this novel ingredient. The prolonged sweetness retention is, demonstrated by the following procedure.

Six subjects chewed each of the two chewing gum compositions described below:

|  | Control | Test |
| --- | --- | --- |
| Gum base | 26.4% | 26.4% |
| Glycerin USP | 5.0% | 5.0% |
| Water, Potable | 2.7% | 2.7% |
| Sorbitol 712 | 64.6% | 64.6% |
| Al-Saccharin Salt | — | 0.12% |
| Saccharin, Acid | 0.1% | — |
| Flavor | 1.2% | 1.2% |

The sweetness perception during chewing of the control batch lasted for 11 minutes while that of the test batch lasted a total of 32 minutes.

All types of chewing gums are contemplated by the invention, thus, slab, stick, shredded and chunk gums are contemplated. Regular chewing gum, bubble gum, hard coated gum and center filled gums are also included. The aluminum salt of saccharin may be incorporated in the chewing gum base, may be added to the surface of the chewing gum piece as a dusting or as a part of the normal surface dusting, may be incorporated in the hard coating of a hard coated gum, and may be included in the center fill mix of a center filled gum.

The use of the aluminum salt of saccharin is not limited to chewing gums. Thus, other applications are also contemplated by the invention. Examples of such application are pressed mints, pressed candies and boiled candies.

Solvates of the aluminum salt of saccharin with nontoxic solvents are also contemplated by the invention. Thus, for example, the hydrate and the ethanolate are contemplated.

Methods of preparing the aluminum salt of saccharin are illustrated by the following examples. Other methods for preparing this novel salt are within the skill of the art and are contemplated by the invention.

EXAMPLE 1

2.04 grams of aluminum isopropoxide is dissolved in 100 ml of hot isopropanol and filtered to remove any insolubles. The filtrate is slowly added to 5.70 grams of saccharin acid dissolved in 200 ml of isopropanol and refluxed for 30 minutes during which time an insoluble, white product is formed. After cooling and filtration the filter cake is washed with isopropanol. The product is air dried. The yield was 3 grams of the aluminum salt of saccharin.

EXAMPLE 2

The method of preparation is the same as that in Example 1 except that 6.84 grams of aluminum isopropoxide in 200 ml of isopropanol is reacted with 11.0 grams of saccharin in 300 ml of isopropanol. The yield was 7.7 grams of the aluminum salt of saccharin drying in air.

EXAMPLE 3

The method of preparation is the same as that in Example 1 except that 10.0 grams of aluminum isopropoxide is reacted with 11 grams of saccharin. After air drying, the yield was 9.5 grams of the aluminum salt of saccharin.

EXAMPLE 4

Aluminum isopropoxide (20 grams) is dissolved in 200 ml of dry toluene and filtered to remove any insolubles. The filtrate is slowly added to 10.0 grams of saccharin and dissolved in 300 ml of isopropanol, and the mixture is refluxed for 30 minutes. No precipitate is formed immediately as in Examples 1, 2 and 3. After standing at room temperature for several days, a white precipitate is formed. The precipitate is filtered and washed with toluene. The product was first dried in air and the at 110° C. in vacuum for four hours. Yield 10.5 grams of the aluminum salt of saccharin.

The aluminum salt of saccharin obtained in each of the above examples all have essentially identical infrared spectra and upon analysis were found to contain 64 to 76.5 percent saccharin (computed as the acid) and 9.4 to 10.4 percent aluminum. This composition does not depend on the ratio of the reactants saccharin and aluminum isopropoxide.

Details of the chemical analyses of the materials isolated in Examples 1 through 4 follow: After brief hydroysis of the salt in dilute acid, suspensions of the solids were analyzed for their aluminum content by atomic absorption and for their saccharin content by HPLC with the following results:

| Solid from Example | % Aluminum | % Saccharin |
| --- | --- | --- |
| 1 | 10.0 | 64.0 |
| 2 | 9.8 | 67.9 |
| 3 | 9.6 | 66.4 |
| 4 (air dried) | 9.4 | 72.5 |
| 4 (dried at 110° C. in vacuum) | 10.4 | 76.5 |

Based on these analyses it was concluded that the prepared solids conformed to the following structure but were contaminated with small amounts of aluminum hydroxide, isopropanol, and/or water:

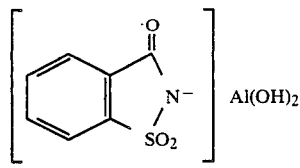

which would show the following theoretical composition:

Aluminum: 11.1%
Saccharin: 74.9%
OH: 14.0%

Substantiation of this structure—which however is not essential to the invention—was obtained as follows:

1. The IR spectra of the compounds prepared in Example 1 through 4 (KRr pellet) show a large peak at 3450 cm$^{-1}$ due to OH stretching. Regardless of how the samples were dried or of the severity of the drying conditions (as high as 110° C. under vacuum for 4 days), the intensity of this OH peak relative to the other major peaks remained unchanged. It is apparent, therefore, that the OH moiety is an integral part of the molecule which could arise by hydrolysis of the aluminum isopropoxy groups which are contained in the presumed intermediate.

2. In order to confirm the presence of these OH-moieties within the molecule, NMR Spectroscopy was conducted on the solid from example 4 and it was found that the proton chemical shift position did not correspond to free water but only to the presence of associated OH-groupings.

3. In order to understand more fully the importance of water in the preparation of the aluminum saccharin salt, the following experiment was conducted:

The following mixture of reagents was added to each of four oven-dried 500 ml glass stoppered volumetric flasks: Aluminum isopropoxide (5 g) dissolved in 100 ml of isopropanol and dried (under vacuum at 110° C. for 18 hours), saccharinic acid (13.5 g) dissolved in 250 ml of dried (with anhydrous MgSO$_4$ overnight) isopropanol. This blend was heated for 30 minutes. Dried (by boiling for 10 minutes) toluene was added to each flask to make 500 ml. Finally distilled water was added as follows:

Flask A: no water
Flask B: 0.09 ml
Flask C: 0.18 ml
Flask D: 0.27 ml within 12 hours, a large amount of white precipitate had formed in Flask D. Flask C contained a modest amount of precipitate plus some crystalline material, while Flask B contained very little of this white precipitate. On the other hand, Flask A remained clear.

The absence of any precipitate in Flask A is a clear indication that the presumed intermediate is soluble in the solvent system employed. Only in the presence of small amounts of water which may have been inadvertently absorbed during the preparation of Examples 1 through 4 is the aluminum salt of saccharin formed. Since aluminum isopropoxide is known to react readily with small amounts of water to form aluminum hydroxide, it was important to determine the saccharin content of the solids isolated from each of the flasks. Not unexpectedly, all solids isolated contained essentially the theoretically required amount of saccharin:

| Samples | % Aluminum | % Saccharin |
| --- | --- | --- |
| Flask B | 8.3 | 69.9 |
| Flask C - white ppt. | 10.6 | 67.3 |
| Flask C - crystalline solids | 9.4 | 73.1 |
| Flask D | 11.6 | 66.3 |
| Theoretical Amount | 11.1 | 74.9 |

4. The samples prepared in Examples 1 through 4 were subjected to I.R. spectroscopy. All I.R. spectra showed remarkably similar patterns, even through the mole ratios of the starting materials were different. Especially noteworthy is the region of 1640–1570 cm$^{-1}$ in which a strong doublet peak corresponding to

stretching, was found. This doublet is absent in the saccharinic acid starting material and indicates that a new chemical compound was formed during the reaction.

5. Finally, x-ray diffraction patterns of aluminum isopropoxide, of saccharinic acid, and the reaction product from Example 4 were compared. The diffraction pattern of the reaction product from Example 4 was shown to be entirely different from the patterns obtained from the starting materials. It is concluded therefrom that the aluminum saccharinate is a new chemical entity.

Preparation of a chewing gum containing the aluminum salt of saccharin of the invention (the Test Sample): In a preheated mixer (50° C.), sorbitol powder is first added and mixed for 2 minutes in order to break up any lumps. In a separate container, gum base is melted with moderate heating (90°–100° C.), and the required amount of aluminum saccharin is added and well blended. The molten gum base-aluminum saccharin mixture is then added to the mixer. Next, the glycerin and water are added and mixed for 5 minutes. The heat is turned off, the flavor is added, and the mass is mixed for an additional 3 minutes. The mass is removed from the mixer, allowed to cool, rolled and cut into pieces using mannitol as a dusting medium.

The Control Sample was prepared in exactly the same manner with the exception that the aluminum saccharin was replaced by saccharinic acid.

In order to demonstrate that the loss of saccharin from the test Sample is significantly slower than that from the Control Sample, chew-out tests were performed as follows: The saccharin contest of pieces of gum was determined and then other samples of the gums were chewed by a group of subjects for 10 minutes. At this time, the boluses were removed from the mouth and assayed for their saccharin contents.

The results tabulated below show that the Test Samples retained almost 50% of their saccharin content after 10 minutes of chewing, while the Control Samples had lost about 75% of their saccharin content. The loss of the sodium salt of saccharin (included for comparison) is almost 100%.

| Sample | Saccharin % Chewed Out |
| --- | --- |
| Control Gum | 75% |
| Test Gum | 51% |
| Commercial Gum with (Na—saccharinate) | 96% |

We claim:

1. A process for preparing the aluminum salt of saccharin which comprises reacting the free acid form of saccharin with an aluminum alkoxide and finally adding a sufficient amount of water to form an aluminum salt of saccharin and recovering an aluminum salt of saccharin having the formula:

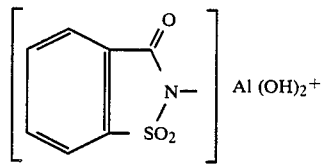

and the following percentage of components:
 (a) Aluminum, 9.4 to 11.1;
 (b) Saccharin (as the acid) 64.0 to 74.9; and
 (c) OH 26.6 to 14, with the following infrared analysis:
 (d) large peak at 3450 cm$^{-1}$; and
 (e) strong doublet at 1640–1570 cm$^{-1}$.

2. The process of claim 1 wherein the aluminum alkoxide has 1 to 6 carbon atoms.

3. The process of claim 1 wherein the aluminum alkoxide is selected from the group consisting of aluminum methoxide, aluminum ethoxide, aluminum isopropoxide and aluminum hexoxide.

4. The process of claim 1 wherein the aluminum alkoxide is aluminum isopropoxide.

* * * * *